(12) United States Patent
Rasheed (10) Patent No.: US 9,447,676 B2
(45) Date of Patent: Sep. 20, 2016

(54) ELECTRONICALLY ACTIVATED UNDERREAMER AND CALLIPER TOOL

(71) Applicant: Wajid Rasheed, Slough (GB)

(72) Inventor: Wajid Rasheed, Slough (GB)

(*) Notice: Subject to any disclaimer, the term of this patent is extended or adjusted under 35 U.S.C. 154(b) by 157 days.

(21) Appl. No.: 13/909,413

(22) Filed: Jun. 4, 2013

(65) Prior Publication Data

US 2013/0306373 A1    Nov. 21, 2013

Related U.S. Application Data

(63) Continuation of application No. 13/161,723, filed on Jun. 16, 2011, now Pat. No. 8,528,668, and a continuation-in-part of application No. 12/966,195, filed on Dec. 13, 2010, now Pat. No. 8,511,404, said application No. 13/161,723 is a continuation-in-part of application No. 12/966,195, filed on Dec. 13, 2010, now Pat. No. 8,511,404, which is a continuation-in-part of application No. PCT/ES2009/070261, filed on Jun. 27, 2009.

(30) Foreign Application Priority Data

Jun. 27, 2008    (GB) .................................. 0811815.0

(51) Int. Cl.
　　*E21B 47/08*    (2012.01)
　　*E21B 10/32*    (2006.01)
　　*E21B 47/00*    (2012.01)
　　*E21B 44/00*    (2006.01)
　　*E21B 47/01*    (2012.01)
　　*E21B 47/12*    (2012.01)
　　*E21B 7/28*     (2006.01)

(52) U.S. Cl.
　　CPC ................. *E21B 47/00* (2013.01); *E21B 7/28* (2013.01); *E21B 10/32* (2013.01); *E21B 44/00* (2013.01); *E21B 47/01* (2013.01); *E21B 47/08* (2013.01); *E21B 47/12* (2013.01)

(58) Field of Classification Search
CPC ...... E21B 47/08; E21B 10/322; E21B 10/32; E21B 44/005; E21B 10/26
See application file for complete search history.

(56) References Cited

U.S. PATENT DOCUMENTS

| 4,665,511 A | 5/1987 | Rodney et al. |
| 4,757,873 A | 7/1988 | Linyaev et al. |

(Continued)

FOREIGN PATENT DOCUMENTS

| JP | 07062967 A | 3/1995 |
| WO | WO0235048 | 5/2002 |

(Continued)

*Primary Examiner* — Kipp Wallace (57) ABSTRACT

An electronically activated tool (50) comprising a tool body, cutter blocks and sensors with means for attachment to a drilling support and rotation so as to permit the simultaneous underreaming and measurement of the diameter of a wellbore (especially in oil and gas drilling) characterized by a means of activation using an electronic signal sent by mud-pulse, fiber-optics, wireless transmission or other means which may also communicate commands and receive data from the underreamer during drilling, at least one radially extendable cutter block (62) incorporating positional sensors adapted to measure the relative position of the cutter block to the tool, at least one calliper means (76) to measure wellbore diameter, all of which are inter-linked by a means of communication using receivers, sensors and microprocessors and a system that optimizes underreaming or expansion (22) by simultaneously comparing and correlating wellbore diameter data (22) and underreaming parameters in real-time or in memory.

19 Claims, 5 Drawing Sheets

(56) References Cited

U.S. PATENT DOCUMENTS

| | | |
|---|---|---|
| 4,791,797 A | 12/1988 | Paske et al. |
| 4,800,537 A | 1/1989 | Mount, II |
| 4,802,145 A | 1/1989 | Mount, II |
| 4,867,264 A | 9/1989 | Siegfried |
| 4,916,400 A | 4/1990 | Best et al. |
| 4,964,085 A | 10/1990 | Coope et al. |
| 4,992,994 A | 2/1991 | Rambow et al. |
| 5,130,950 A | 7/1992 | Orban et al. |
| 5,175,429 A | 12/1992 | Hall, Jr. et al. |
| 5,214,251 A | 5/1993 | Orban et al. |
| 5,317,111 A | 5/1994 | Orban et al. |
| 5,341,345 A | 8/1994 | Warner et al. |
| 5,354,956 A | 10/1994 | Orban et al. |
| 5,414,673 A | 5/1995 | Scherbatskoy |
| RE34,975 E | 6/1995 | Orban et al. |
| 5,459,697 A | 10/1995 | Chin et al. |
| 5,469,736 A | 11/1995 | Moake |
| 5,515,336 A | 5/1996 | Chin et al. |
| 5,753,812 A | 5/1998 | Aron et al. |
| 5,987,385 A | 11/1999 | Varsamis et al. |
| 5,995,447 A | 11/1999 | Mandal et al. |
| 6,002,639 A | 12/1999 | Birchak et al. |
| 6,021,093 A | 2/2000 | Birchak et al. |
| 6,038,513 A | 3/2000 | Varsamis et al. |
| 6,088,294 A | 7/2000 | Leggett, III et al. |
| 6,125,079 A | 9/2000 | Birchak et al. |
| 6,213,250 B1 | 4/2001 | Wisniewski et al. |
| 6,366,531 B1 | 4/2002 | Varsamis et al. |
| 6,552,962 B1 | 4/2003 | Varsamis et al. |
| 6,564,899 B1 | 5/2003 | Arian et al. |
| 6,672,163 B2 | 1/2004 | Han et al. |
| 6,693,554 B2 | 2/2004 | Beique et al. |
| 6,747,570 B2 | 6/2004 | Beique et al. |
| 6,817,229 B2 | 11/2004 | Han et al. |
| 6,891,777 B2 | 5/2005 | Pabon et al. |
| 6,899,197 B2 | 5/2005 | Arian et al. |
| 6,957,145 B2 | 10/2005 | Spross |
| 6,987,463 B2 | 1/2006 | Beique et al. |
| 6,995,500 B2 | 2/2006 | Yogeswaren |
| 7,036,363 B2 | 5/2006 | Yogeswaren |
| 7,046,165 B2 | 5/2006 | Beique et al. |
| 7,075,215 B2 | 7/2006 | Yogeswaren |
| 7,173,542 B2 | 2/2007 | Beique et al. |
| 7,364,007 B2 | 4/2008 | Garcia-Osuna et al. |
| 7,367,392 B2 | 5/2008 | Duong et al. |
| 7,389,828 B2 | 6/2008 | Ritter et al. |
| 7,418,865 B2 | 9/2008 | Griffiths et al. |
| 7,460,435 B2 | 12/2008 | Garcia-Osuna et al. |
| 7,513,147 B2 | 4/2009 | Yogeswaren |
| 7,587,936 B2 | 9/2009 | Han |
| 7,658,196 B2 | 2/2010 | Ferreri et al. |
| 7,775,215 B2 | 8/2010 | Hassler, Jr. et al. |
| 7,775,966 B2 | 8/2010 | Dlugos et al. |
| 7,814,782 B2 | 10/2010 | DiFoggio |
| 7,844,342 B2 | 11/2010 | Dlugos, Jr. et al. |
| 7,927,270 B2 | 4/2011 | Dlugos et al. |
| 7,932,834 B2 | 4/2011 | Beique et al. |
| 7,950,451 B2 | 5/2011 | Alberty |
| 8,016,744 B2 | 9/2011 | Dlugos et al. |
| 8,028,767 B2 | 10/2011 | Radford et al. |
| 8,057,492 B2 | 11/2011 | Ortiz et al. |
| 8,066,629 B2 | 11/2011 | Dlugos |
| 8,276,689 B2 * | 10/2012 | Giroux et al. ............... 175/171 |
| 2005/0194182 A1* | 9/2005 | Rodney et al. ............... 175/24 |
| 2005/0211470 A1 | 9/2005 | Jeffryes |
| 2006/0249307 A1 | 11/2006 | Ritter et al. |
| 2007/0005316 A1 | 1/2007 | Paez |
| 2007/0205022 A1 | 9/2007 | Treviranus et al. |
| 2007/0235199 A1 | 10/2007 | LoGiudice et al. |
| 2008/0035376 A1* | 2/2008 | Freyer ............... 175/45 |
| 2008/0053707 A1 | 3/2008 | Martinez et al. |
| 2008/0128175 A1 | 6/2008 | Radford et al. |
| 2008/0186805 A1 | 8/2008 | Han |
| 2009/0090554 A1 | 4/2009 | Sugiura et al. |
| 2009/0266544 A1 | 10/2009 | Redlinger et al. |
| 2009/0294173 A1 | 12/2009 | Laird et al. |
| 2010/0089583 A1 | 4/2010 | Xu et al. |
| 2010/0139981 A1 | 6/2010 | Meister et al. |
| 2010/0282511 A1 | 11/2010 | Maranuk et al. |
| 2011/0203849 A1 | 8/2011 | Radford et al. |
| 2011/0226531 A1 | 9/2011 | Jones |

FOREIGN PATENT DOCUMENTS

| | | |
|---|---|---|
| WO | WO2004074630 A1 | 9/2004 |
| WO | WO2006083738 A1 | 8/2006 |

\* cited by examiner

ELECTRONICALLY ACTIVATED UNDERREAMER AND CALLIPER TOOL

This application is a continuation of copending U.S. patent application Ser. No. 13/161,723, filed Jun. 16, 2011 and entitled "ELECTRONICALLY ACTIVATED UNDERREAMER AND CALLIPER TOOL", and is a continuation-and-part of copending U.S. patent application Ser. No. 12/966,195, filed Dec. 13, 2010, and entitled "DRILLING TOOL, APPARATUS AND METHOD FOR UNDERREAMING AND SIMULTANEOUSLY MONITORING AND CONTROLLING WELLBORE DIAMETER", which is a continuation-and-part of International Application number PCT/ES09/70261, filed Jun. 27, 2009 and entitled "DRILLING TOOL AND METHOD FOR WIDENING AND SIMULTANEOUSLY MONITORING THE DIAMETER OF WELLS AND THE PROPERTIES OF THE FLUID", and claims priority to and the benefit of GB 0811815.0, filed Jun. 27, 2008 and entitled "EXPANSION AND CALLIPER TOOL", the entireties of which applications are hereby incorporated by reference as if fully set forth herein.

FIELD OF THE INVENTION

This invention relates to an electronically activated expansion tool that is capable of enlarging and measuring borehole and tubular diameters, especially those drilled to construct wellbores in the oil and gas industry. The expansion operation is verified by data provided by the tool and this is used to optimise underreaming to meet cementing or casing tolerances. Such data may be the measurement of the underreamed wellbore diameter using an acoustic calliper or a mechanical calliper, or it may be the expandable cutter block position. The tool finds particular use as an underreaming and calliper tool, but can also be configured without cutting elements to provide downhole centralization, directional stabilisation, or as a means for expanding tubulars.

It is to be understood that the term 'expansion' as used herein refers to the capacity of the tool to expand outwardly towards and against the interior wall or walls of a passage, such as a borehole, especially a wellbore, or a tubular, and then to apply pressure or a cutting action against the wall or walls. It is not always essential that the passage itself be expanded, since the tool can be used for centralisation or stabilisation or like purposes without necessarily expanding the passage.

When constructing an exploration or production well, numerous downhole operations are conducted to drill and measure a borehole so that it meets the desired well-plan. Drilling itself may utilise a reamer to ensure that the hole diameter that has been drilled by the bit is maintained within the given tolerance. The hole diameters drilled by the bit and perfected by the reamer are substantially the same as the maximum cutting diameter of a reamer, which is fixed and is substantially the same as the bit diameter. This maximum cutting diameter is defined by the pass-through diameter of any restriction in the borehole above the operating location.

In contrast to a reamer, an underreamer is used to enlarge a borehole beyond its original drilled size. Enlargement is typically done below a restriction in the borehole, and the cutting diameter of an underreamer is always greater than that of the pass-through diameter of the restriction. Additionally, an underreamer is provided with activation and deactivation modes and mechanisms for extending and retracting cutting elements to ensure effective underreaming once it has passed below the restriction.

Measurement may involve the acquisition and communication to surface of various types of wellbore data such as drilling dynamics, resistivity, porosity, permeability, azimuth, inclination and borehole diameter or rugosity, formation dips or bedding angles.

Measurement itself occurs in two modes, either wireline or logging-while-drilling. Wireline is by far the most common measurement technique and is performed as a separate and consecutive activity to drilling involving the conveyance of measurement tools on a wire or cable. Wireline callipers use a plurality of fingers to take borehole diameter measurements. However, wireline callipers can only take measurements in an axial direction. Due to this limitation, they can only be used after drilling otherwise the rotational and impact forces of drilling would cause them to break. Hence a separate calliper run is required after drilling to measure borehole diameter.

Logging-while-drilling or measurement-while-drilling tools may acquire various data from the wellbore. For drilling dynamics measurement-while-drilling is the preferred means of acquiring drilling data such as vibration. Acoustic callipers may be incorporated within logging tools. As they can be rotated, acoustic callipers may be used while drilling to acquire measurement data. However, almost all logging tools are configured as complete systems and are only available at very high cost and are not used in all wells worldwide. Further they also suffer from limitations in applications with slide drilling, where a downhole motor rotates the bit and drags the drillstring and bottom-hole assembly, or BHA. Or in Rotary steerable applications where they are configured near to the bit. Therefore, the location of the sensor is within the BHA below the underreamer. It can only give readings after the section has been underreamed.

In the case of underreaming, measurements are taken a posteriori i.e. after underreaming, which means a separate calliper run and at times further corrective runs to attain the desired wellbore diameter.

Presently, activation of underreamers is limited to hydraulic or mechanical means based on internal flow restrictions configure as venturis or 'ball-drop' or 'shear pins'. In the case of flow, pumps are brought up to a pre-determined level which causes internal pressure to build-up and exceed the annular pressure. This causes a mechanical component to move and activate the tool. In the case of weight, the method relies on the use of shear pins which are rated to a given weight bearing and sheared with a mechanical force. Due to fluctuations in stand pipe pressure and the subsequent downhole pressures, pressure restrictions are not always the ideal means for activation. Further, drop-balls restrict any fishing or retrieval of components below the underreamer which means that highly sophisticated logging-while-drilling equipment such as nuclear sources may be lost in the hole. Shear pins are load bearing and therefore can present problems due to the progressive weakening the shear pin undergoes each time its bearing surface is subject to vibration or movement. This occurs until the true shear value is reduced and results in premature activation of the underreamer in the casing and damage to the wellbore as well as increased cost and delay.

The present invention allows for electronic activation of the expansion and calliper tool as well the ability to communicate commands and receive data from the tool during drilling. This provides an advantageous, independent and reliable means of activation which is not dependent on hydra-mechanical forces and allows the underreamer status to be controlled on command.

The present invention may be activated by means of electronic signal sent by a built-in mud-pulse telemetry means or a third party telemetry means. It may also be activated using other means such as fibre-optic or wireless transmission.

As will become apparent the tool and related apparatus may be configured in any number of ways so that object of the invention which is to reduce uncertainty and downtime is achieved.

BACKGROUND OF THE INVENTION

Oil and gas accumulations are found at depth in different geological basins worldwide. Exploration and production of such accumulations rely on the construction of a well according to a well plan.

Various well types exist and are defined according to usage such as wildcats or those used in exploration; delineation; and production and injection. Variations in well profile exist also according to vertical, slant, directional and horizontal trajectories. Each differs according to the oil company's objectives and the challenges that a given basin presents from the surface of the earth or the ocean to the hydrocarbon reservoir at a given underground depth.

Engineering challenges are related to the location of the well-site such as onshore or offshore, seawater depths, formation pressures and temperature gradients, formation stresses and movements and reservoir types such as carbonate or sandstone. To overcome these challenges, a highly detailed well plan is developed which contains the well objective, coordinates, legal, geological, technical, well engineering and drilling data and calculations.

The data is used to plot a well profile using precise bearings which is designed in consecutive telescopic sections—suface, intermediate and reservoir. To deliver the well objective and maintain the integrity of well over its lifecycle, a given wellbore with multiple sections and diameters is drilled from surface. Although there are many variants, a simple vertical well design could include a surface or top-hole diameter of 17½" (445 mm), intermediate sections of 13⅝" (360 mm) and 9⅝" (245 mm) narrowing down to the bottom-hole diameter of 8½" (216 mm) in the reservoir section.

Each consecutive section is 'cased' with the specified diameter and a number of metal tubes placed into the wellbore according to the length of the section. Each must be connected to each other after which they are cemented into the appropriately sized hole with a given tolerance. In this way, a well is constructed in staged sections, each section dependent on the completion of the previous section until the well is isolated from the formation along the entire distance from surface to the reservoir.

Scarcity of oil and gas is driving oil and gas companies to explore and develop reserves in more challenging basins such as those in water-depths exceeding 6,000 ft (1830 m) or below massive salt sections. These wells have highly complex directional trajectories with casing designs including 6 or more well sections. Known in the art as 'designer' or 'close tolerance casing' wells, these wells have narrow casing diameters with tight tolerances and have created a need to enlarge the wellbore to avoid very narrow diameter reservoir sections and lower production rates.

Therefore, the bottom-hole assemblies that are needed to drill these wells routinely include devices to underream the well-bore below a given casing diameter or other restriction. In this way, underreamed hole size has become an integral part of well construction and there is now an increased dependence on underreaming to meet planned wellbore diameters.

After underreaming, the underreamer is tripped out from the borehole and replaced by a calliper, which is an instrument for measuring the internal dimensions of the bore either mechanically, typically by means of extending fingers that contact the inside of the bore, or by acoustic or other echo-based sounding techniques.

Previously, the underreamer and calliper have been considered as two separate tools, each involved in distinct functions. Typically, an underreaming run could take 24 hours, after which a further 24 hours would be required for preparation of the calliper run. A further 24 hours could be taken in the calliper run before knowledge could be gained of actual wellbore diameters. The time-lag between underreaming and calliper measurements, therefore could easily exceed 48 hours depending on the depths involved. If the actual hole diameter did not match the planned diameter, casing tolerances would not be met and therefore a corrective run would be required and the whole cycle of underreaming and calliper measurements would need to be repeated.

In other applications such as tubular expansion casing or increased cementing thicknesses, the tolerances between the enlarged well-bore and the expanded tubular are very close. Variations of 1" (25 mm) diameter can lead to the failure of the well construction activity.

Notwithstanding, the limitations of the prior art are overcome with the present invention, the wellbore construction process will continue to depend on given wellbore diameters for the placement of casing in a wellbore with a given tolerance which is determined by the required cementing thickness.

Consequently, where an undergauge (below tolerance) diameter goes undetected this would potentially jeopardize the wellbore construction activity. The present invention avoids this by measuring and verifying wellbore diameter and underreamer status and if either were insufficient, the tool performs automated diagnostics and may alert the user as required.

To those skilled in the art, it is known that underreaming generates uncertainty as to the activation status of the underreamer. This is because underreamers do not provide for clear activation status as described in Patent GB 2465505 which is incorporated herein as a reference.

The present invention is differentiated in this aspect as it provides for activation electronically as well as real-time verification of activation status by means of electronic signal which would enable a driller to activate a tool with certainty and eliminate reliance on hydra-mechanical activation. This would reduce time spent on activation as well as permit the exchange of data with the tool and surface.

The data may be transmitted in real-time by means of data transfer (mud pulse telemetry, fibre-optic or other) or maybe stored in memory and downloaded at a later time. The present invention would make underreamer status known in a clear manner and optimize underreaming operations thereby reducing failures and improving drilling efficiency and wellbore construction.

It is unsatisfactory to depend on indirect indicators such as whether cutter blocks are open or closed or whether fluid pathways are open and a pressure spike is seen at the rig floor to indicate activation. Such indicators do not provide actual measurements of the underreamed well-bore underreamed nor do they provide verification of underreaming erformance; they simply give information on the mechanical or hydraulic status of an aspect of the tool which may or may not lead to the desired well diameter.

To those skilled in the art, it is known that the industry relies on even more rudimentary and time-consuming indicators of verification such as an increase in drilling torque as cutters interact with the formation or even pulling up the drill-string and underreamer to the previous hole size in order to see whether the top-drive stalls as the bottom-hole assembly gets stuck due to the expanded tool. Or by drilling a pilot hole section with the underreamer deactivated and pulling back into the pilot hole.

Therefore, the prior art does not lend itself to a reliable or certain means of measuring and verifying underreamed wellbore diameters in real-time or memory mode.

Further the prior art perpetuates drilling inefficiencies due to the uncertainty of the actual status of the underreamer.

Further the prior art generates time-consuming cycles of entry and exit into the well-bore.

Further the prior art relies on pressure restrictions or weight for activation.

Further the prior art does not detect variations in well-bore in real-time.

Further the prior art does not automatically troubleshoot undergauge hole or malfunction.

SUMMARY OF THE INVENTION

The present invention has for a principal object to provide an improvement on the prior art wherein the actual diameter of the underreamed hole is measured directly in real time, that is to say simultaneously with, or immediately after, an expansion operation.

The invention seeks to meet the need for an integrated underreamer and calliper equipped with wellbore diameter measurement means and electronic activation, which provides real time performance verification and automated troubleshooting. This has not been forthcoming in the prior art due to design limitations inherent in the hydraulic or weight activation and the prior art cutter block retention mechanisms or prior art mechanical calliper designs.

Usage of the electronic activation means may further be provided as a means of communication with the tool wherein commands or data may be sent or received from the tool.

The present invention seeks to integrate and automate underreaming and calliper measurement offering performance verification and eliminates the need for separate calliper runs and minimizes the need for corrective underreaming runs by providing real-time data which allows the driller to respond earlier thereby saving time and money. This would allow measurement of required diameters for casing and cementing tolerances and thereby reduce uncertainty and improve wellbore construction.

It is thus an object of the present invention to provide callipers integrated with an underreamer, enabling the integrated device to give immediate measurement of the accuracy of the wellbore-widening operation and, if it is found insufficient or undergauge, to automatically detect and diagnose the faults, and to repeat underreaming until a satisfactory result is achieved in real-time.

Although underreaming is a principal route to wellbore enlargement, the invention envisages alternative enlargement means similarly integrated with calliper measurement of the enlarged bore. These alternative means could include bicentre bits, fixed wing bits, eccentric underreamers and expandable bits.

It is a further object to provide a tool capable of simultaneously conducting well-bore enlargement, taking calliper measurements preferably by an acoustic echo-pulser and sensor, and verifying performance through a processor arrangement that uses sensor data to detect undergauge hole and conducts diagnostics according to a logic circuit in order to ensure the underreamer is functioning correctly. If the corrective steps have been taken and the calliper indicates that the planned hole diameter is still not being delivered an alert signal may be sent to the rig-surface or to the location of the operating engineer so that further remedial action can be taken, such as tool replacement. A memory mode may store sensor information that can be downloaded at surface when the tool is retrieved, or sent to the surface by telemetry.

The tool may also be configured as a standalone tool with a built-in link to a mud-pulse telemetry system or alternatively the tool may be linked to a third party mud-pulser in the case of measurement while drilling or logging while drilling usage to allow real-time monitoring of the underreaming operation (cutter-block position and acoustic calliper data simultaneously). One or more echo-pulsers may be optimally spaced in order to emit a number of sound waves during a given time period which are reflected back by the near wellbore or by the far formation in the case of a cavernous formation and picked up by the sensor. The distance may be calculated using the travel time and speed of return.

In a preferred embodiment the integrated tool or separate housings of the tool may incorporate electronic activation means from the surface to downhole where an electrical signal is used in part and converted to binary code and pulsed as pressure pulses through a fluid medium in the drill-pipe or annulus or to a transducer in the drill-pipe or annulus containing a decoder that converts the pressure pulses back into electrical signals.

In a further embodiment the electronic signal is transmitted from surface to the tool downhole via a hard wire or fibre optic cable.

In yet a further embodiment the electronic signal is transmitted from surface and converted to radio waves and transmitted by a short hop to a transponder where it is received and converted back into electronic signal.

A keyway may provide a channel for wiring from the sensors to the processor and transponder. The wiring can be used to transmit acoustic data retrieved by the acoustic sensors, as well as positional data from the mechanical blocks, to the processor and transponder. The keyway may be sealed and filled with a means to absorb vibration such as silicon gel or grease and to maintain wires in position.

The transponder converts data so that it can be transmitted and is linked to the in-built or $3^{rd}$ party mud-pulser which transmits the data to surface using a series of binary codes at a given frequency using drilling fluid as means of mud pulsing. Other means of data transfer may be used such as wireless transmission short hop using radio frequency or other electro-magnetic pulses. This allows up and downlink of the tool in order to receive and transmit data and commands. At surface a transducer may be incorporated within a decoder housing which decodes the binary code and may link to the driller's terminal or may be yet further transmitted by satellite or other means to a remote operations centre.

The preferred embodiment of the invention provides for an electronically activated wellbore underreaming tool (50), which is particularly applicable in oil and gas wells, comprising a tool body, cutter blocks and calliper with means for attachment to a drilling support and rotation so as to permit the simultaneous underreaming and measurement of the diameter of an wellbore characterized by at least one radially extendable cutter block (62) at least one calliper means (76 or 66, 64) to measure wellbore diameter and at least one radially extendable stabiliser block (63), an electronic means of activation, all of which are interlinked by a means of communication using receivers, sensors and microprocessors; a system that delivers a desired wellbore diameter (22) by simultaneously comparing and correlating measured wellbore diameter and activated cutter block position (62); inter-linked by means of sensors and microprocessors.

In further embodiments the invention provides for the incorporation of positional sensors adapted to measure the relative position of the cutter block to the tool, or to measure the relative position of the radially extendable stabiliser block relative to the tool.

The support to the tool may typically be a drill string or an extended length of coiled tubing, as used in downhole operations in oil and gas fields.

The tool body is typically a cylindrical high grade steel housing adapted to form part of a bottom-hole assembly (BHA). Thus the means for attaching the tool body to the support, whether it is a drill string or coiled tubing, may comprise a screw thread provided on the tool body which is engageable with a drill collar. The attachment to the drill string need not be direct, but may be indirect, as there will typically be many different functional elements to be included in the long and narrow BHA, and the arrangement of the successive elements may vary. The lower end of the BHA may be the drill bit, or a bull nose, and in between there may or may not be a means for directional control such as a rotary steerable system.

The wellbore underreaming is achieved by means of a cutter block or a plurality of cutter blocks. The set of cutters may comprise a cutter block carrying a plurality of cutter elements directed outwardly of the tool body. The cutter block may be received within the tool body in a cutter block chamber having an open mouth, and the cutter may be extendable from the chamber through the chamber mouth with the cutter elements projecting from the tool body, and retractable back into the chamber. The cutter elements may be polydiamondcrystalline inserts, or other inserts according to requirements. The tool body may be provided with an internal duct (90) receiving a source of drilling fluid flowing to an external nozzle adjacent the set of cutters.

The tool also has a housing for expandable stabilising elements which can be connected by means of a connection to the body. This can act to stabilize the tool against the wellbore wall during underreaming and measurement and if so required, increase or expand the diameter of a tubular or casing.

Other embodiments of the tool may provide for separate housings and sections for calliper means, mud-pulser means and stabilising means so that the separate housings and sections may be connected by means of a connection and inter-linked by means of sensors and processors for use in oil and gas wellbore underreaming, drilling or expansion operations.

It is to be noted that the description herein of the structure and operation of cutter or expansion blocks is applicable generally, irrespective of function, except to the extent that cutter inserts may be provided specifically for underreaming purposes and removed for expansion purposes of expandable casing.

The microprocessor may provide a means of control (68) and is programmed to receive data from the calliper means on the underreamed wellbore diameter as well as the cutter block positional data from the sensor which is placed on each cutter block and its housing. The microprocessor may therefore control the extension and retraction positions of the cutter block based on a logic circuit programmed within the microprocessor. In this way, an integrated tool which is capable of diagnosing under-performance and correcting it may be realised. The dimension data may prompt for tests and checks on the effective deployment of the expansion elements, may trigger a repeated cycle of expansion, and may provide data to a surface monitor to signal an opportunity for operator intervention.

The tool normally comprises a plurality of such cutter blocks, arranged symmetrically around the tool. Two cutter blocks would be on opposite sides of the tool, three blocks would be separated by 120 degrees, four by ninety degrees, and six by sixty degrees. In operation, the underreaming tool is typically rotated on the drill string as well as being moved axially along the wellbore.

In accordance with a particularly preferred aspect of the invention, the tool body is provided with an internal duct for directing drilling fluid from a source to an external nozzle adjacent the cutter elements. The source of drilling fluid may be the drill-string or other support for the tool, and the aforementioned through passage for the flow of drilling fluid from the drill string to the drill bit. In each case, the nozzle provides a fluid flow that can help to keep the cutters clean and prevent the build-up of clogging debris from the reaming operation, remove such material altogether from the underreaming zone, and provide a cooling and lubricating function for the cutters. In one preferred aspect the present invention incorporates a non-mechanical means of measurement which is practically applicable and may be an acoustic calliper.

Thus, in the case of an underreaming tool with acoustic calliper means, acoustic reflections from an echo-pulser may be transmitted to a sensor and calculated as distance by multiplying time by speed. The processor correlates the borehole data from the distance allowing for variations in fluid or formation caverns. The processor uses this data to correlate whether the pre-programmed wellbore diameter is actually being underreamed and measured. The underreamed wellbore diameter callipers are generally located above the underreamer but in an alternative configuration may be placed within the cutter block itself among the most radially extended cutting elements.

The skilled man will readily appreciate that other procedures may be implemented by the logic circuit within the processor, which can be programmed to cover other scenarios.

BRIEF DESCRIPTION OF THE DRAWINGS

Embodiments of the invention are illustrated by way of non-limiting examples in the accompanying drawings, in which.

DETAILED DESCRIPTION OF THE INVENTION

Figure 1:
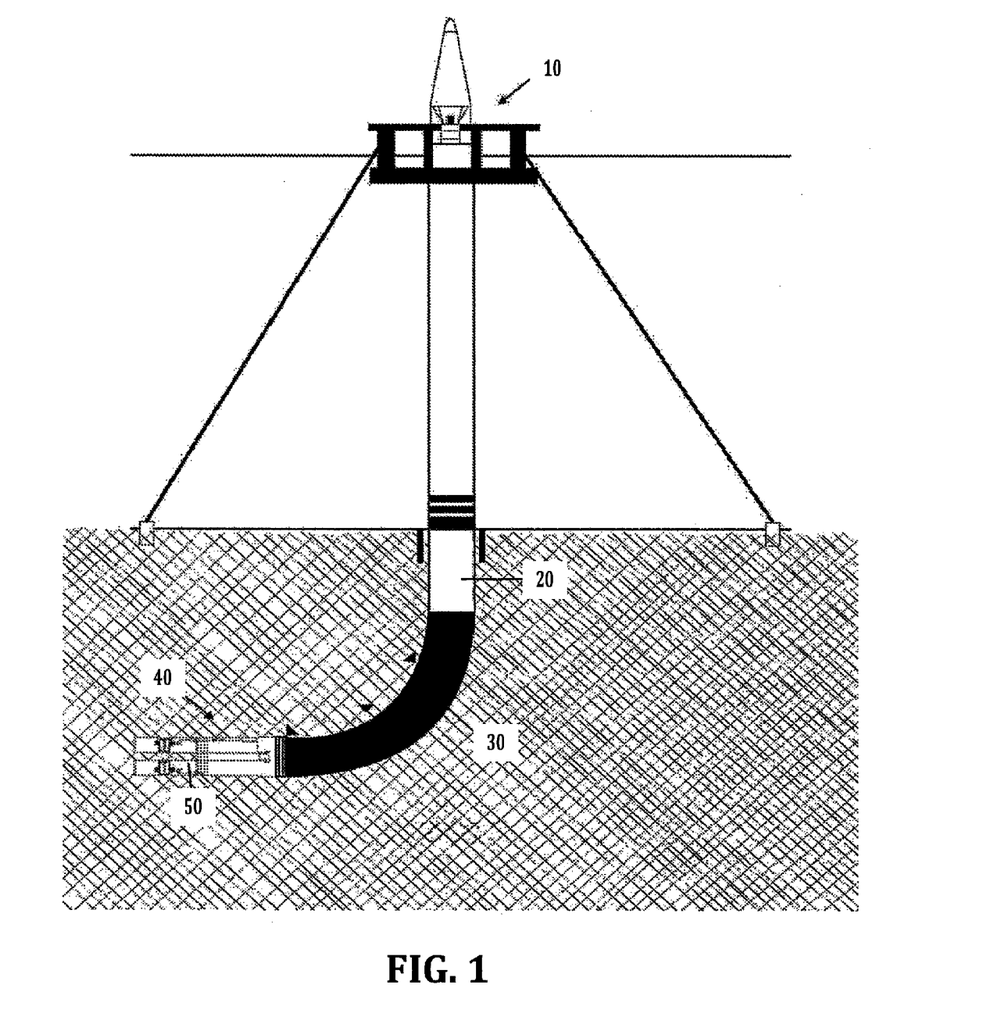
FIG. 1 is a general diagrammatic view of an oil or gas well showing surface structures and the underground wellbore, with a tool in accordance with the invention as part of a bottomhole assembly.

As shown in FIG. 1, an exemplary exploration or production rig comprises a surface structure 10 at the wellhead, a wellbore 20, and a drill string 30 in the wellbore with a bottom-hole assembly 40 at its lower end. The bottom-hole assembly includes an underreamer and calliper tool 50 in accordance with the invention, and a drill-bit (not shown).

Figure 2A:
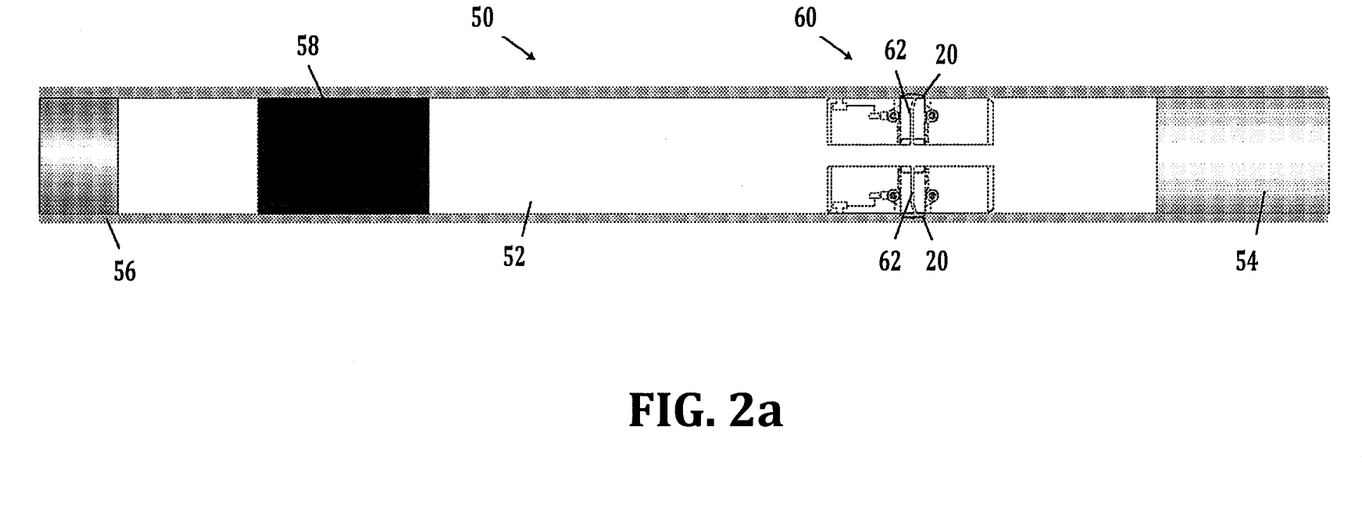
FIG. 2a is a side elevation, part cut away to show the expansion elements in a deactivated state, of the tool of FIG. 1.
Figure 2B:
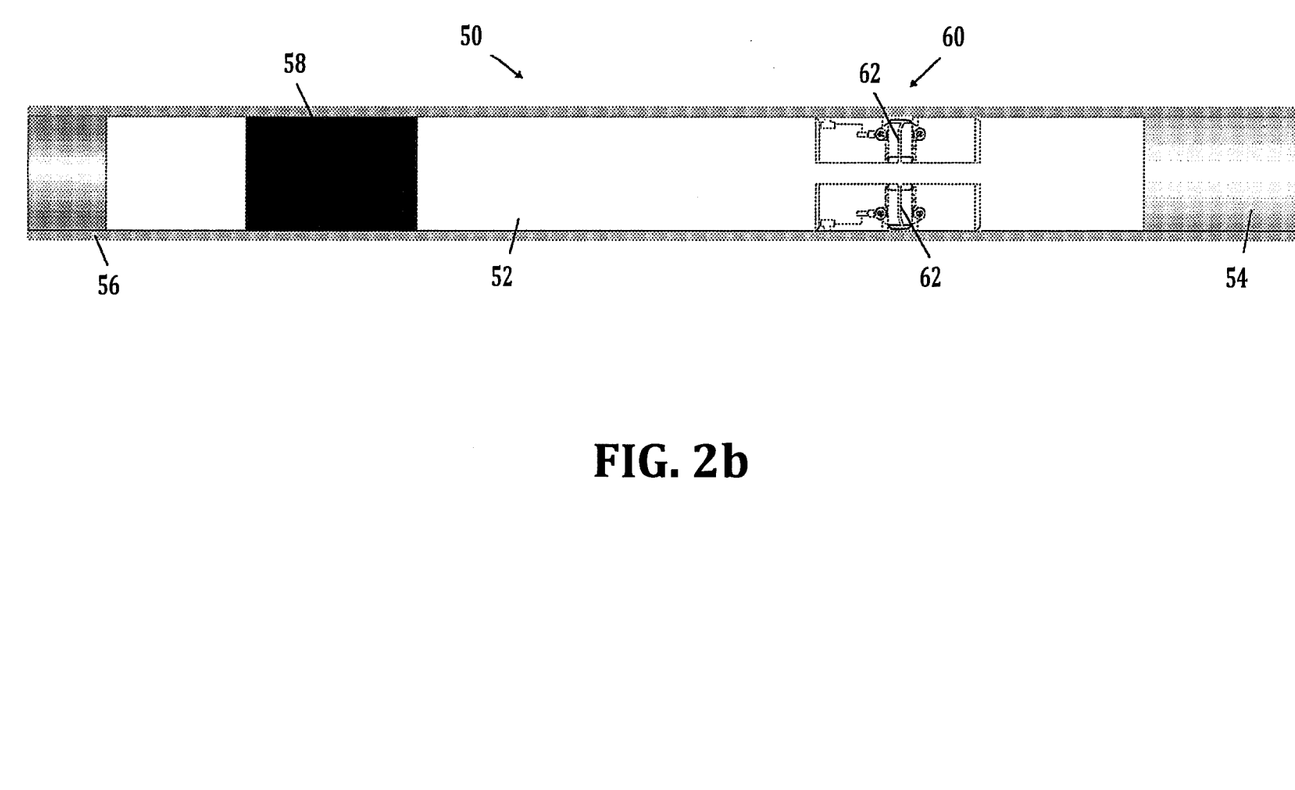
FIG. 2b is a side elevation corresponding to FIG. 2a showing the expansion elements in an activated state.

The integrated expansion and sensing tool 50 is illustrated in FIGS. 2a and 2b, and comprises a tubular steel body 52 provided with a drilling collar 54 at its downhole end and a mud-pulser 56 at its other end, which is adapted to be engaged by a further drill collar (not shown) to connect it other elements of the bottom-hole assembly 40, and then to the drill string 30.

The tool body also carries a calliper 76 and an expansion element assembly 60 between the calliper and the drill collar 54. The expansion element assembly 60 comprises a number of expansion blocks 62 disposed symmetrically, radially around the tool body 52, and in the deactivated condition shown in FIG. 2a the blocks are withdrawn into the tool body, but in the activated condition shown in FIG. 2b the blocks are extended beyond the tool body against the wellbore 20.

Figure 3:
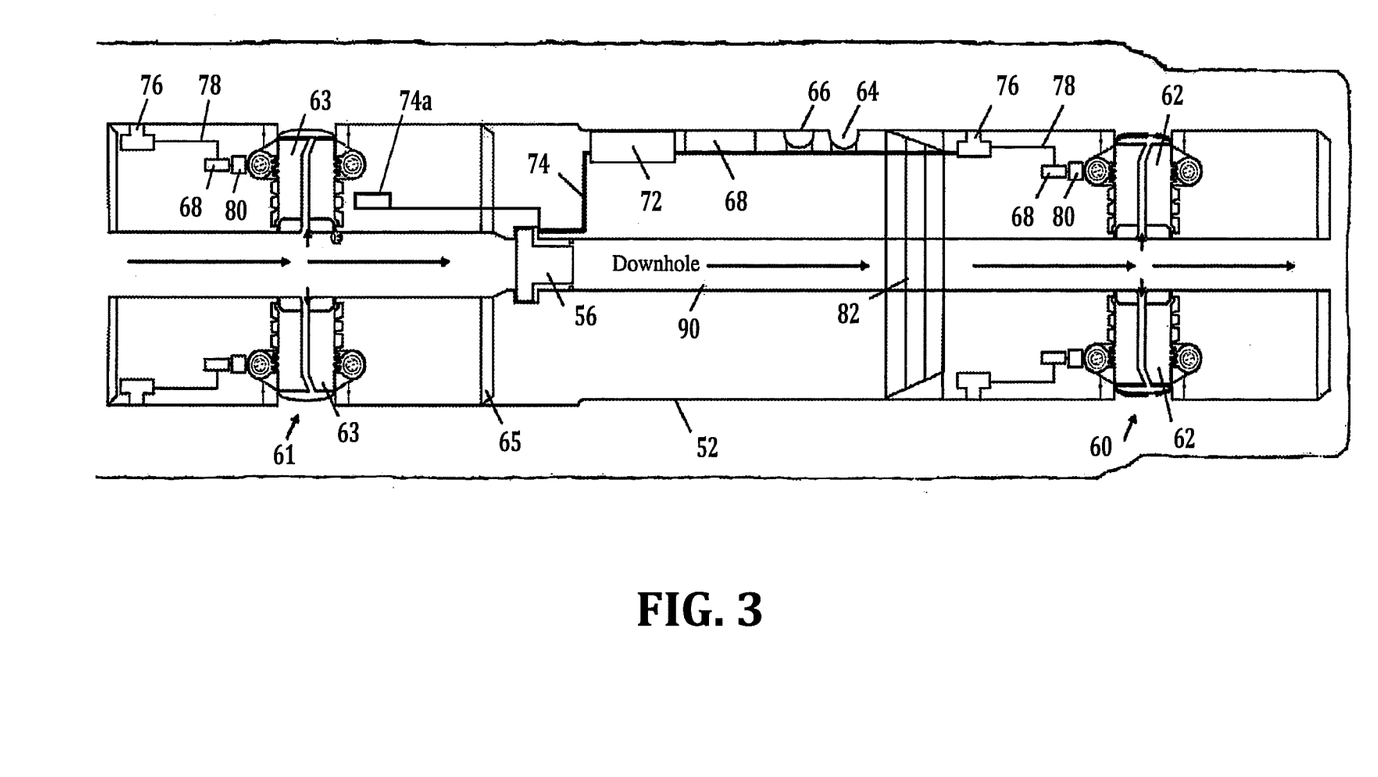
FIG. 3 is a diagrammatic cross section through an underreaming and sensing tool in accordance with the invention similar to that shown in the previous Figures, but having an additional stabiliser section at the trailing uphole end.

FIG. 3 illustrates diagrammatically the aforementioned elements of the tool 50, together with a stabiliser section 61. As will become apparent the tool sections can be connected directly or indirectly to each other according to requirement. In this way, a plurality of embodiments may be outlined within the scope of the invention including variations such as the stabiliser section connected to the underreamer or the stabiliser may simply house a caliper means with or without a mud-pulser means or the stabiliser section may house underreaming blocks.

As the sensor means 76 indicated in FIG. 3, further sensors may be incorporated in 64 or 66. Data is processed using a micro-processor 68, shown in two alternative locations, that correlates data from the sensor 66 to detect a critical condition or simply store data for further analysis. The tool is also programmed and automated to conduct diagnostics according to a logic circuit or diagnostic program stored in processor 68 in order to ensure the underreamer is functioning correctly. Once corrective steps have been taken, and if drilling dynamics are still not optimised, an alert signal is sent via the mud-pulser 56 to the rig-surface 10 or to a remote operator so that further remedial action such as the replacement of the BHA 40 can be considered. A memory module associated with processor 68 may store sensor information that can be downloaded at surface when the tool is retrieved, or sent to the surface by telemetry through mud-pulser 56.

The tool is provided with a built-in link to a data transfer system 56 which may also serve to monitor real-time wellbore diameter. One or more callipers are placed in 76, 64 or 66 are spaced within the tool body 52 in order to measure wellbore diameter in real-time or memory.

As further shown in FIG. 3, a keyway 74 provides a channel for wiring from the sensors 66 to the processor 68, and also to a transponder 72. The wiring is used to transmit data retrieved by the sensors to the processor and transponder. The keyway may be sealed and filled with a means to absorb vibration and maintain wires in position such as silicon gel or grease.

The transponder 72 converts data from microprocessor 68 so that it can be transmitted to surface 10 and is linked to the mud-pulser 56 which transmits the data to surface using a series of binary codes at a given frequency using drilling fluid as means of mud pulsation. Other means of data transfer may be used such as wireless transmission, short hop using radio frequency or electro-magnetic pulses.

FIG. 3 also shows an alternative location for a sensor, in housing 66 or 64 connected to wiring in keyway 74, and further wiring 78 to alternative processor location 68 FIG. 3 also shows a central axial through passage 90 for the flow of drilling fluid through the whole bottom-hole assembly 40.

The sensor means 76, 58, or 64, 66, is typically housed within the tool body 52 above the underreamer 60, but in a variation a calliper 76, 122 may be located within the expansion block.

The tool body 52 is a cylindrical high grade steel housing adapted to form part of a bottom-hole assembly (BHA) 40. FIG. 3 shows an internal connection 82 joining two parts of tool body 52. At the leading downhole end of the tool is a section housing the cutter blocks 62. Connection 82 joins this to a central section housing measurement and control functions. A further section 61 at the uphole end, joined by connection 65, houses stabiliser blocks 63 which are constructed and housed substantially identically to the underreamer components generally designated 60, except that in place of cutter elements on cutter blocks there is at least one surface which is hard faced or coated with a hard abrasion-resistant material. A similar construction can be used to expand a deformable bore, such as a steel tubular. The means for attaching the tool body to a drill string or coiled tubing comprises a screw thread (not shown) provided on the tool body which is engageable with a drill collar (not shown).

In this alternative configuration the tool is configured, in addition to underreaming capacity, with the underreaming tool body incorporating hard facing cutter blocks to act as a stabiliser. The hard facing acts to prevent cutter abrasion while reaming or stabilising the underreamed hole. This eliminates some of the problems associated with loss of directional control due to the undergauge stabiliser above the underreamer.

In yet another configuration the tool is provided with a stabilizer directly or indirectly connected to the underreamer housing where the stabiliser housing may also be provided with electronic activation means and may be linked to a calliper means so that the stabilizer and calliper is used to perform essentially the same function as the integrated underreamer and calliper except that the stabiliser is stabilising the tool and BHA.

The stabiliser may be directly or indirectly connected to the underreamer and hard-wired accordingly so as to ensure the mud-pulser may transmit data to surface. The tool may be provided with a mud-pulser as a standalone tool or the mud pulser itself may be provided by a third party as would be the case when a measurement while drilling or logging while drilling suite of tools is located in the BHA below the present invention. The hard wiring configuration of the tool may be changed to suit such an application.

The tool normally comprises a plurality of such cutter blocks 62, arranged symmetrically around the tool. Two cutter blocks are on opposite sides of the tool, three blocks are separated by 120 degrees, four by ninety degrees, and six by sixty degrees. In operation, the underreaming tool 50 is typically rotated on the drill string as well as being moved axially along the wellbore.

Figure 4:
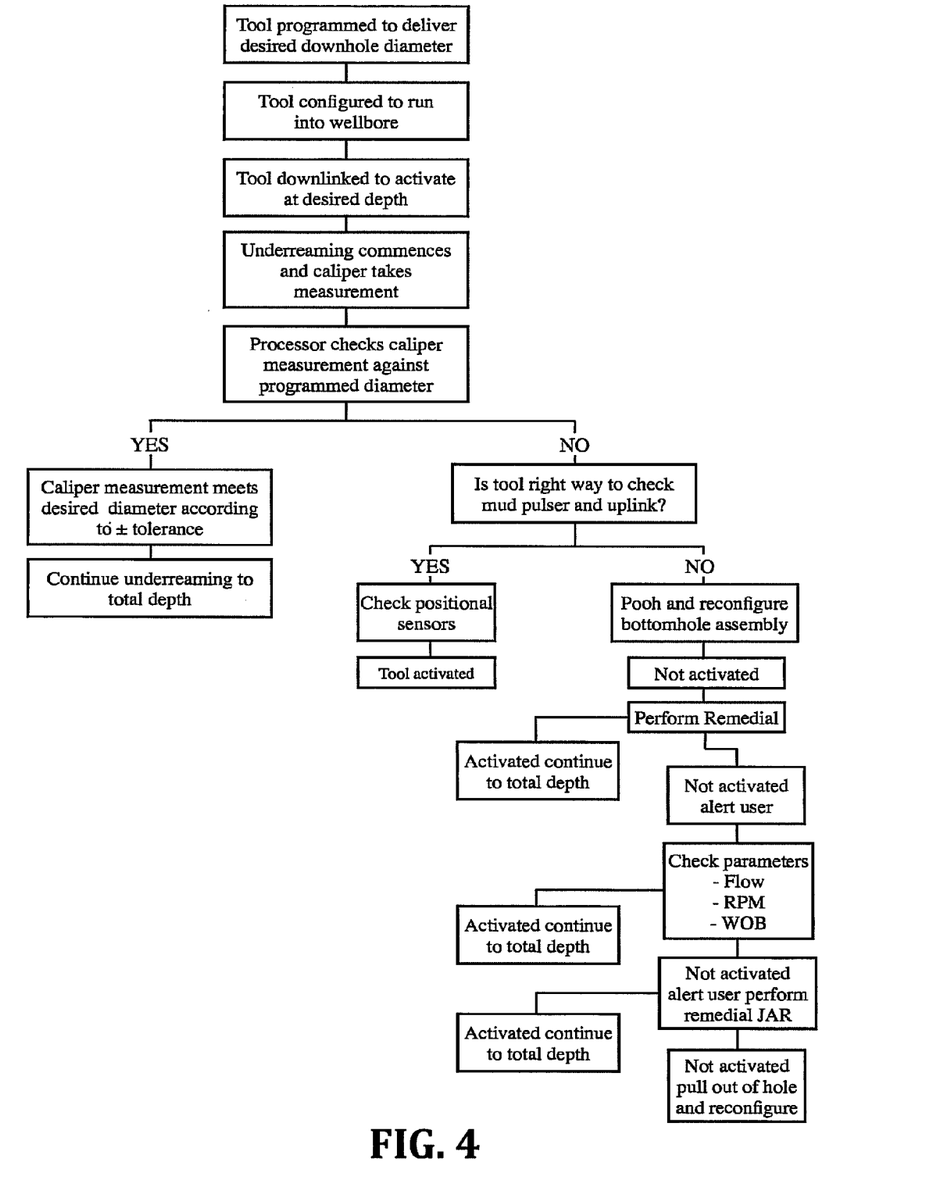
FIG. 4 is an exemplary logic circuit showing the reduction of uncertainty and automated diagnostics that the tool provides

As shown in the FIG. 4 logic diagram, said logic program may be configured in any number of ways so as to optimize performance. An exemplary configuration involves the circuit to first cross check the cutter block positional data from the positional strip (which may be magnetic) which is placed on each cutter block and signals to a sensor within the cutter pinion teeth or housing. The signal that is constantly created by the magnetic strip is at its strongest when the block is fully extended and the strip and sensor are aligned. In this way, it can be seen whether the block has actually been extended. If the block has been extended yet the caliper data shows that the actual wellbore is below the planned wellbore, the microprocessor alerts the user by means of mud pulse telemetry to check operational parameters such as drilling fluid pump rates or surface rotational speed. Other examples of the logic within the micro-processor 68 can be programmed by the skilled man to cover many other scenarios.

As noted above, the invention provides a method of operating an underreaming tool to enlarge a borehole to a target dimension below a restriction, which comprises locating a tool as claimed in any one of the preceding claims in a borehole on a drill string below a restriction, activating the tool electronically, extending the set of cutters to an underreaming diameter greater than the restriction, rotating the tool and moving it axially along the borehole on the drill string, measuring wellbore diameter by the calliper means, and continuing the underreaming operation until the target depth is achieved.

In addition to the above, the tool may be provided with a calliper means and cutter extension control means responsive to dimension data received from the calliper means.

Those skilled in the art will appreciate that the examples of the invention given by the specific illustrated and described embodiments show a novel underreaming tool and system and method for underreaming using electronic activation, with numerous variations being possible. These embodiments are not intended to be limiting with respect to the scope of the invention. Substitutions, alterations and modifications not limited to the variations suggested herein may be made to the disclosed embodiments while remaining within the ambit of the invention.

The invention claimed is:

1. A method of closed loop reaming to provide a borehole with a predetermined dimension, comprising providing a rig in contact with a reamer and a processor linked to a calliper measuring borehole dimension, thereby providing caliper data,
sensing a relative position of extendable cutter blocks using a magnetic position sensor thereby providing extendable cutter block positional data,
wherein said cutter blocks are housed within a tool body and extendable from said tool body and said magnetic sensor remains housed within a tool body when said cutter blocks are extended,
wherein the processor makes a comparison between said calliper data, and said extendable cutter block positional data, wherein the processor sends an alert to a user in response to the comparison to check operational parameters in order to to ensure that the borehole is accurately provided with the predetermined dimension, wherein a user is capable of making a user comparison between said caliper data, said extendable cutter block positional data, and said predetermined borehole dimension.

2. The method of claim 1 wherein the relative position of the cutter blocks is monitored at surface.

3. The method of claim 1 wherein the relative position of the said cutter blocks is detected downhole.

4. The method of claim 1 wherein at least one signal related to said cutter block position is recorded by the user or processor.

5. The method of claim 1 using electronic or mechanical signals to activate said cutter blocks.

6. The method of claim 1 further comprising sensing a property from one of a group comprising flow, rotation, weight, sound transit time, density, and hydraulic force using a properties sensor.

7. The method of claim 1 wherein at least two extendable cutter blocks are located in longitudinally separate housings.

8. The method of claim 1 further comprising at least one extendable element.

9. The method of claim 1 further comprising at least one extendable stabilizer.

10. A method of reaming below a restriction in a borehole comprising: providing a drill-bit and an extendable tool to increase a diameter of a borehole greater than a diameter of a drill-bit after passing through the restriction, said tool being activated to extend extendable blocks on the extendable tool to increase the size of said borehole to a desired diameter greater than that of the restriction and drill bit, further providing a processor linked to a calliper measuring borehole dimension, rotating said tool and moving it axially along the wellbore;
measuring a reamed borehole diameter using the calliper,
measuring an extendable block position using a magnetic position sensor,
wherein the processor makes a comparison between said measured reamed borehole diameter and the measured extendable block position, wherein the processor further sends an alert to a user in response to the comparison to check operational parameters in order to control underreaming and deliver the desired borehole diameter, wherein a user is capable of making a user comparison between said caliper data, said extendable cutter block positional data, and said predetermined borehole dimension.

11. The method of claim 10 where monitoring is performed in real time or memory.

12. The method of claim 10 where the calliper is mechanical.

13. The method of claim 10 wherein a surface transducer is used to detect the extendable block position signal.

14. The method of claim 10 wherein said drill-bit is replaced by bull-nose or expandable bit.

15. The method of claim 10 further comprising recording a signal related to alignment of a nozzle.

16. The method of claim 10 further comprising checking an underreaming property from one of a group comprising flow, rpm, weight, and hydraulic force.

17. A method for increasing borehole diameter below a restriction in a borehole comprising a drill-bit and an extendable tool to increase a diameter of the borehole to a size greater than a diameter of the drill-bit after passing through the restriction, said extendable tool being activated to extend extendable blocks on the extendable tool to increase said borehole diameter to a size greater than that of the restriction and drill bit, rotating said tool and moving it axially along the wellbore while flowing fluid through the tool; providing a position sensor to measure an extendable cutter block position and a calliper to measure the reamed borehole diameter and wherein a processor makes a comparison between the measured extendable cutter block position and the measured reamed borehole diameter and alerts a user in response to the comparison to check weight on the cutter blocks, torque on the cutter blocks, or a flow rate of fluid through the tool, wherein a user is capable of making a user comparison between said caliper data, said extendable cutter block positional data, and said predetermined borehole dimension.

18. The method of claim 17 using said position sensor to detect an extendable block position.

19. The method of claim 17 wherein the calliper comprises an acoustic caliper and providing a fluid properties sensors to determine sound transit time and calibrate said acoustic caliper.

* * * * *